(12) United States Patent
Renshaw

(10) Patent No.: US 6,258,794 B1
(45) Date of Patent: Jul. 10, 2001

(54) TREATMENT OF MENTAL CONDITIONS INCLUDING DEPRESSION

(75) Inventor: Perry F. Renshaw, Arlington, MA (US)

(73) Assignee: The McLean Hospital Corporation, Belmont, MA (US)

( * ) Notice: Subject to any disclaimer, the term of this patent is extended or adjusted under 35 U.S.C. 154(b) by 0 days.

(21) Appl. No.: 09/690,286

(22) Filed: Oct. 17, 2000

Related U.S. Application Data

(60) Provisional application No. 60/231,052, filed on Sep. 8, 2000, and provisional application No. 60/170,646, filed on Dec. 14, 1999.

(51) Int. Cl.[7] ............................ A61K 31/70; A61K 31/52
(52) U.S. Cl. .............................................. 514/46; 514/263
(58) Field of Search ........................................ 514/46, 263

(56) References Cited

U.S. PATENT DOCUMENTS

| | | | |
|---|---|---|---|
| 5,032,594 | 7/1991 | Takehiko et al. | 514/267 |
| 5,047,534 | 9/1991 | Peet et al. | 544/267 |
| 5,064,947 | 11/1991 | Peet et al. | 536/26 |
| 5,187,162 | 2/1993 | Marangos et al. | 514/46 |
| 5,236,908 | 8/1993 | Grubber et al. | 514/46 |
| 5,250,284 | 10/1993 | Krongrad | 424/9 |
| 5,329,007 | 7/1994 | Peet et al. | 544/262 |
| 5,688,774 | 11/1997 | Jacobson et al. | 514/46 |
| 5,734,052 | 3/1998 | Peet et al. | 544/273 |
| 5,763,597 | 6/1998 | Ugarkar et al. | 536/27.13 |
| 5,919,789 | 7/1999 | Dyke et al. | 514/263 |
| 6,103,702 | 8/2000 | Law | 514/46 |

OTHER PUBLICATIONS

Barankiewicz et al., "Regulation of adenosine concentration and cytoprotective effects of novel reversible adenosine deaminase inhibitiors," *J. Pharm. Exp. Ther.* 283(3):1230–1238 (1997).

Britton et al., "Site and event specific increase of striatal adenosine release by adenosine kinase inhibition in rats," *Neuosci. Lett.* 266(2):93–96 (1999).

Christensen et al., "Abnormal cerebral metabolism in poly–drug abusers during early withdrawl: a [31]P MR spectroscopy study," *Magn. Reson. Med.* 35:658–663 (1996).

Deicken et al., "Basal ganglia phosphorous metabolism in chronic schizophrenia," *Am J. Psychiatry* 152:126–129 (1995).

Eigler et al., "Suppression of TNF–α production in human mononuclear cellsby an adenosine kinase inhibitor," *J. Leukoc. Biol.* 68:97–103 (2000).

Golembiowska et al., "Adenosine kinase inhibitors augment release of adenosine from spinal cord slices," *Eur. J. Pharmacol.* 307(2):157–162 (1996).

Hebb et al., "Co–administration of adenosine kinase and deaminase inhibitors produces supra–additive potentiation of N–methyl–D–asparate–evoked adenosine formation in cortex," *Eur. J. Pharmacol.* 344(2–3):121–125 (1998).

Jiang et al., "Adenosine kinase inhibition protects brain against transient focal ischemia in rats," *Eur. J. Pharmacol.* 320(2–3):131–137 (1997).

Kaplan et al., "Adenosine kinase inhibitors attenuate opiate withdrawal via adenosine receptor activation," *Eur. J. Pharmacol.* 362(1):1–8 (1998).

Kowaluk et al., "Characterization of the effects of adenosine kinase inhibitors on acute thermal nociception in mice," *Pharmacol. Biochem. Behav.* 63(1):83–91 (1991).

Moore et al. "Lower levels of nucleoside triphosphate in the basal ganglia of depressed subjects: a phosphorous–31 magnetic resonance spectroscopy study," *Am. J. Psychiatry* 154:116–118 (1997).

Picano et al., "European stroke prevention study–2 results: serendipitous demonstration of neuroprotection induced by endogenous adenosine accumulation?," *Trends Pharmacol. Sci.* 19(1):14–16 (1998).

Renshaw et al., "Basal ganglia choline levels in depression and response to fluoxetine treatment: an in vivo proton magnetic resonance spectroscopy study," *Biol. Psychiatry* 41:837–843 (1997).

Tatisumak et al., "Delayed treatment with an adenosine kinase inhibitor, GP683, attenuates infarct size in rats with temporary middle cerebral artery occlusion," *Stroke* 29:1952–1958 (1998).

Wang et al., "The effect of GP683, an adenosine kinase inhibitor, on the desflurane anesthetic requirement in dogs," *Anesth. Analg.* 85(3):675–680 (1997).

Wiesner et al., "Adenosine kinase inhibitors as a novel approach to anticonvulsant therapy[1]," *J. Pharmacol. Exp. Ther.* 289:1669–1677 (1999).

Volz et al., "P magnetic resonance spectroscopy in the frontal lobe of major depressed patients," *Eur. J. Psychiatry Clin. Neurosci.* 248:289–295 (1998).

*Primary Examiner*—Raymond Henley, III
(74) *Attorney, Agent, or Firm*—Clark & Elbing, LLP

(57) ABSTRACT

The invention provides methods of treating a patient suffering from depression by increasing circulating adenosine levels in the patient. The invention also features diagnostic methods for depression which involve measuring purine or NTP resonance intensity.

18 Claims, 1 Drawing Sheet

TREATMENT OF MENTAL CONDITIONS INCLUDING DEPRESSION

CROSS REFERENCE TO RELATED APPLICATIONS

This application claims priority to U.S. Ser. No. 60/231,052, filed Sep. 8, 2000, which is a continuation-in-part of U.S. Ser. No. 60/170,646, filed Dec. 14, 1999.

STATEMENT AS TO FEDERALLY SPONSORED RESEARCH

This invention was funded by grant RO1-MH48866. The government may have certain rights in the invention.

BACKGROUND

Major depression has been associated with both global and regional decreases in cerebral blood flow and glucose metabolism, assessed using emission tomography methods (reviewed in 1). In parallel, single voxel phosphorus-31 MRS has been used to document decreased levels of beta and total NTP in the basal ganglia (2; −16% and −6%) and the bilateral frontal lobes (3; −17% and −8%). Although these results are somewhat surprising, they are consistent with observations obtained from the cerebral cortex of polysubstance abusers (5; −10% and −7%) and decline in beta NTP in the basal ganglia of schizophrenics (4; −11%), disorders which have also been associated with sustained cerebral hypometabolism.

Over the last several years, van Zijl and colleagues (6,7,8) have clearly demonstrated that a $^1$H MRS resonance which arises from purines may be detected in the range 7.8–8.8 PPM using short echo times. This resonance arises primarily from adenosine phosphates, with a smaller contribution from NAA at 7.8–8.0 PPM.

SUMMARY

We have reanalyzed the low field purine resonance in short echo time STEAM spectra acquired from the basal ganglia of depressed and healthy subjects (9). As a subset of these subjects also participated in a $^{31}$P MRS study (2), the relationship between the $^1$H MRS purine-resonance and the $^{31}$PNTP resonance was assessed. Finally, as all of the depressed study subjects were enrolled in a standardized clinical trial, $^1$H MRS purine measures were correlated with the clinical response to treatment.

All MR spectra were obtained using a GE Signa 1.5T MR scanner (4.8 operating system). Proton spectra were acquired from an 8 cm$^3$ voxel centered the left caudate and putamen. STEAM acquisition parameters were TR=2 sec., THE=30 msec., 256 averages, 1024 data points, and 2500 Hz spectral width. Phosphorus-31 spectra were acquired from a 45 cm$^3$ volume encompassing the bilateral basal ganglia. ISIS acquisition parameters were TR=3 sec., flip angle=90 degrees, acquisition delay=350 microsec, 512 averages, 1024 data points, and 2500 Hz spectral width. All subjects completed the $^1$H MRS protocol while 13 depressed and 18 control subjects completed the $^{31}$P MRS study.

Spectra were analyzed using SA/GE (described in 2 and 9) by a single analysis who was blind to clinical data. The intensity of the purine resonance was determined by integration of the 7.53–8.52 PPM region and separately normalized to the intensity of the resonances for NAA, Cre, and Cho. Images used for voxel prescription were segmented into gray matter, white matter, and CSF using MRX

RESULTS

Figure 1B:
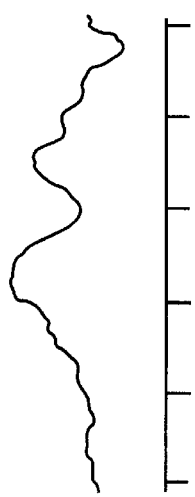
FIGS. 1B–1D are the summed and averaged low field $^1$H spectra for the comparison subjects (N=22) (FIG. 1B), the depressed subjects who did not respond to treatment (N=21) (FIG. 1C), and the depressed subjects who respond to treatment (N=17) (FIG. 1D). All spectra were scaled to the Cre resonance (Cre intensity=1) prior to summation.
Figure 1C:
Figure 1D:
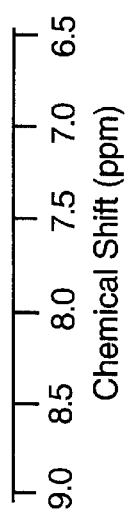
Figure 1A:
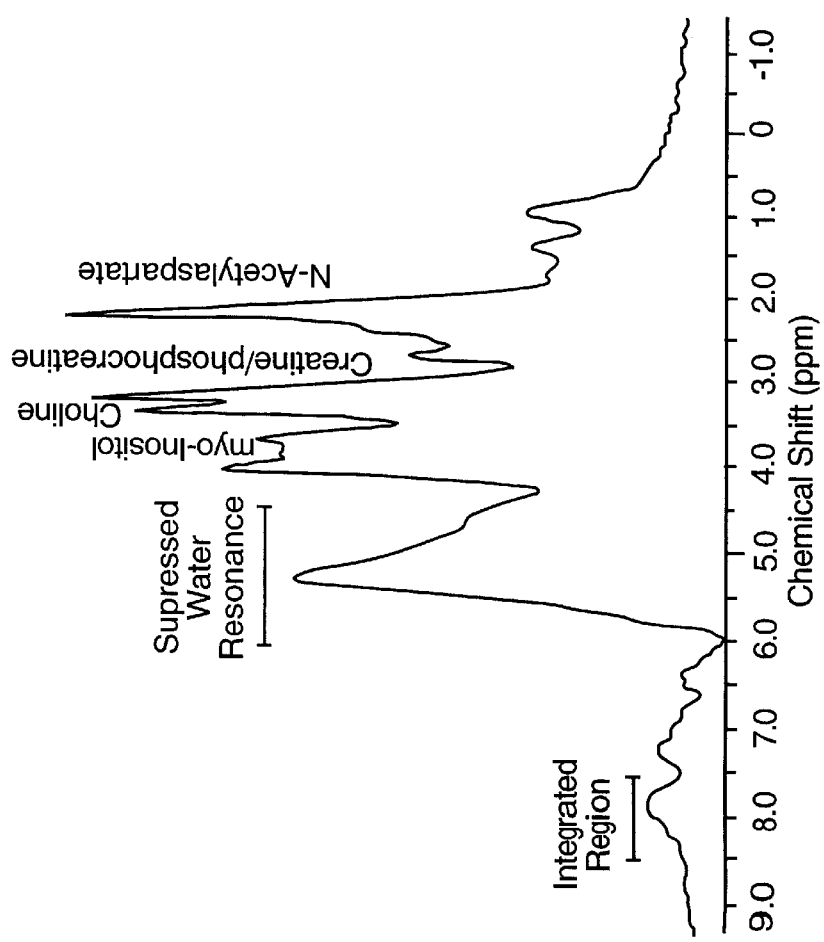
FIG. 1A is the averaged $^1$H spectra for the comparison subjects.

For the comparison subjects, the intensity of the purine resonance, expressed as P/NAA, P/Cre, and P/Cho, was strongly and negatively correlated with voxel gray matter content r=−0.596, −0.662, and −0.490, respectively (p=0.009, 0.003, and 0.04, respectively).

After controlling for the effects of voxel tissue content, P/NAA, P/Cre, and P/Cho were all significantly lower in the depressed treatment responders than in the depressed non-responders or the controls (t=2.80, 1.71, 1.85; p=0.01, 0.09, 0.07) (table 1). In both the responders and the non-responders, lower P/NAA, P/Cre, and P/Cho ratios were associated with lower levels of depression (HDRS scores; r=0.312, 0.243, 0.314; p=0.05, 0.14, 0.05).

For the depressed subjects, beta NTP resonance was statistically lower in the depressed treatment responders than in the depressed non-responders (F=11.32; p=0.006). In addition, P/NAA, P/Cre, and P/Cho tended to correlate with the intensity of the beta NTP resonance r=0.46, 0,59, and 0.48; p=0.13, 0.042, and 0.12).

TABLE 1

MRS Metabolite Ratios (Mean ± SD)

|  | Comparison | Nonresponders | |
|---|---|---|---|
|  | (n = 22) | (n = 21) | (n = 17) |
| P/NAA | 0.24 ± 0.09 | 0.25 ± 0.11 | 0.18 ± 0.09 |
| P/Cre | 0.40 ± 0.19 | 0.42 ± 0.15 | 0.34 ± 0.12 |
| P/Cho | 0.53 ± 0.24 | 0.58 ± 0.23 | 0.47 ± 0.30 |
| b-NTP | 15.4 ± 3.45 | 13.0 ± 1.34 | 10.5 ± 1.33 |

DISCUSSION

To the best of our knowledge, this is the first report on purine resonance intensities in proton MR spectra from human subjects with a brain disorder. As a retrospective study, optimal acquisition parameters for detecting the purine resonance (8) could not be employed. Nonetheless, the present results suggest that decreased brain purines may observed in treatment-responsive depressed subjects and that these $^1$H MRS measures correlate well with $^{31}$P MRS measures of beta-NTP. More generally, these observations suggest that $^1$H MRS may provide clinically relevant insights into cerebral energetics with a substantial increase in sensitivity relative to $^{31}$P MRS measures.

The World Health Association has reported that by the year 2020, major depression will be the second most debilitating disease to affect mankind, following only ischemic heart disease (12). To the extent that altered cerebral adenosine metabolism is associated with major depression, compounds which modify adenosine metabolism may provide important new therapeutic strategies (13, 14).

Accordingly, in one aspect, the invention features a method of treating a patient suffering from depression, in particular, major depression (also known as clinical depression), by administering to the patient an effective amount of a pharmaceutical composition containing a compound that inhibits adenosine uptake or breakdown, or a compound that, in vivo, releases or provides adenosine, combined with a pharmaceutically acceptable carrier substance, e.g., physiological saline or sterilized water. In one preferred embodiment, the depressive illness is bipolar disorder or manic depression.

The above-described methods can also be used to treat other brain disorders that are characterized by cerebral hypometabolism i.e., brain disorders in which cells of the brain exhibit decreased oxygen utilization and/or glucose metabolism due to decreased levels of adenosine. Such disorders include, without limitation, schizophrenia, substance abuse (and in particular, stimulant abuse such as cocaine and amphetamine dependence), and Huntington's Disease. We believe that increasing that brain levels of cytosolic adenosine will provide the effective therapy for these disorders because of our observation that brain levels of cytosolic adenosine compounds or complexes (e.g. ATP+, ADP+, AMP+, and adenosine) are decreased in persons diagnosed with depression.

Compounds are known that are capable of increasing adenosine levels by all of the mechanisms contemplated by the invention. Thus, for example, adenosine uptake can be inhibited by a number of known compounds, including propentofylline, a compound that inhibits adenosine uptake (described in U.S. Pat. No. 5,919,789, hereby incorporated by reference). Another known compound that inhibits adenosine uptake is EHNA.

Other useful compounds that can be used to increase brain adenosine levels are those that inhibit enzymes that breaks down adenosine (e.g., adenosine deaminase, adenosine kinase). Examples of adenosine kinase inhibitors include 5'amino-5'-deoxyadenosine (15), 5'-deoxy-5-iodotubercidin (15), 5'-iodotubericidin (15), iodotubericidin (16), iodotubericidin, GP515 (17), 4-(N-phenylamino)-5-phenyl-7-(5'-deoxyribofuranosyl)pyrrolo[2,3-d]pyrimidine (also called GP683) (15, 18), and derivatives thereof. Other adenosine kinase inhibitors include, but are not limited to, those described by Wiesner et. al. (15). An example of an adenosine deaminase inhibitor is 2'-deoxycoformycin.

Additionally, adenosine receptor antagonists, which inhibit activation of adenylyl cyclase (cAMP) by adenosine receptors, may be used to increase adenosine levels. In one embodiment, the adenosine receptor antagonists is theophylline or 8-(p-sulfophenyl)theophylline (15). Finally, administering compounds that contain adenosine or precursors of adenosine, which are released as adenosine in vivo, can also be used.

Prior to administering the brain adenosine-increasing compounds of the invention, it is preferable to conduct tests that positively diagnose the brain chemistry disorder of the patient.

In another aspect of the invention, any of the above-described brain adenosine-increasing compounds can be used to treat patients suffering from decreased cognitive performance caused by adenosine-related cerebral hypometabolism.

The compounds of the invention can be administered by any standard means for administering therapeutic compounds, including oral, sublingual, intravenous, and administration into the cerebrospinal fluid. Dosages and timing of administration can be determined using routine methods for such determination.

In yet another aspect, the invention provides a diagnostic method for depression. This method involves performing proton or phosphorous MRS resonance imaging on a human subject to measure the intensity of purine resonance and/or NTP resonance. A lower than normal purine resonance intensity or NTP resonance intensity indicates depression. In a preferred embodiment, the lower intensity indicates depression that can be treated with a therapy that raises the level of circulating adenosine.

References

1. Drevets, *Ann. Rev. Med.* 49, 341–361, 1998.
2. Moore et al., *Am. J. Psychiatry* 154, 116–118, 1997.
3. Volz et al., *Eur. J. Psychiatry Clin. Neurosci.* 248, 289–295, 1998.
4. Deicken et al., *Am. J. Psychiatry* 152, 126–129, 1995.
5. Christensen et al., *Magn. Reson. Med.* 35, 658–663, 1996.
6. Van Zijl et al;, *Magn. Reson. Med.* 29, 381–385, 1993.
7. Decanniere et al., *Magn. Reson. Med.,* 34, 343–352, 1995.
8. Mori et al., *Magn. Reson. Med.,* 40, 36–42, 1998.
9. Renshaw et al., *Biol. Psychiatry* 41, 837–843, 1997.
10. Hamilton, *J. Neurol. Neurosurg. Psychiatry* 23, 56–62, 1960.
11. Kikinis et al., *J. Magn Reson. Imaging* 2, 619–629, 1992.
12. Murray et al., *The global burden of disease.* Harvard Press, 1996.
13. Barankiewicz et al., *J. Pharm. Exp. Ther.* 283, 1230–1238, 1997.
14. Picano et al., *TIBS* 19, 14–16, 1998.
15. Wiesner et al., *J Pharmacol. Exp. Ther* 289, 1669–1677, 1999.
16. Kaplan et al., *Eur. J. Pharmacol.* 362, 1–8, 1998.
17. Eigler et al., *J. Leukoc. Biol.* 68, 97–103, 2000.
18. Tatlisumak et al. *Stroke* 29, 1952–1958, 1998.

All publications mentioned in this specification are herein incorporated by reference to the same extent as if each independent publication was specifically and individually indicated to be incorporated by reference.

What is claimed is:

1. A method of treating a patient suffering from depression, said method comprising administering to said patient a pharmaceutical composition comprising (i) a compound that inhibits adenosine uptake or breakdown in vivo, or a compound that contains adenosine or an adenosine precursor, wherein the compound is processed in vivo to increase the circulating adenosine level in the patient; and (ii) a pharmaceutically acceptable carrier.

2. A therapeutic method for hypometabolic brain disorders comprising:
   (a) identifying a compound that inhibits adenosine uptake or breakdown in vivo or provides adenosine in vivo;
   (b) carrying out a diagnostic test to identify a patient suffering from a brain hypometabolic disorder associated with decreased brain adenosine levels; and
   (c) administering to said patient a pharmaceutical composition comprising said compound admixed with a pharmaceutically acceptable carrier.

3. The method of claim 2, wherein said patent suffers from depression, brain-affecting substance dependence, or a cerebral hypometabolic disorder.

4. The method of claim 3, wherein said depression is bipolar disorder or manic depression.

5. The method of claim 2, wherein said compound inhibits adenosine deaminase.

6. The method of claim 2, wherein said compound inhibits adenosine kinase.

7. The method of claim 6, wherein said adenosine kinase inhibitor is selected from the group consisting of 5'-amino-5'-deoxyadenosine, 5'-deoxy-5-iodotubercidin, 5'-iodotubericidin, iodotubericidin, 4-(N-phenylamino)-5-phenyl-7-(5'-deoxyribofuranosyl)pyrrolo[2,3-d]pyrimidine, and GP515.

8. The method of claim 2, wherein said compound is an adenosine receptor antagonist.

9. The method of claim 2, wherein the patient suffers from schizophrenia.

10. The method of claim 2, wherein the patient suffers from Huntington's Disease.

11. A therapeutic method comprising:
  (a) performing diagnostic testing on a patient to determine whether the patient is suffering from depression, brain-affecting substance dependence, or a cerebral hypometabolic disorder; and
  (b) if said diagnostic testing indicates that the patient is suffering from one of said disorders, administering to said patient an effective amount of a chemical compound selected from the group consisting of:
    (i) a compound that inhibits adenosine breakdown in vivo
    (ii) a compound that inhibits adenosine uptake in vivo
    (iii) a compound that contains adenosine or an adenosine precursor, wherein said compound is processed in vivo to increase the circulating adenosine level in said patient.

12. The method of claim 11, wherein the patient suffers from major depression and the compound inhibits adenosine uptake.

13. The method of claim 11, wherein the patient suffers from brain stimulant dependence and the compound inhibits adenosine uptake.

14. The method of claim 12, wherein the compound is EHNA.

15. The method of claim 12, wherein the compound is EHNA.

16. The method of claim 12, wherein said compound is propetofylline.

17. A diagnostic method for depression, said method comprising performing proton or phosphorous MRS resonance imaging on a human subject to measure the intensity of purine resonance and/or NTP resonance, wherein a lower than normal purine resonance intensity or NTP resonance intensity indicates depression.

18. The method of claim 17, wherein said lower intensity indicates depression that can be treated with a therapy that raises the level of circulating adenosine.

* * * * *